United States Patent [19]
Duschl

[11] 4,454,541
[45] Jun. 12, 1984

[54] CHARGE COUPLED DEVICE BASED BLEMISH DETECTION SYSTEM AND METHOD

[75] Inventor: Robert A. Duschl, Lancaster, Pa.
[73] Assignee: RCA Corporation, New York, N.Y.
[21] Appl. No.: 388,038
[22] Filed: Jun. 14, 1982
[51] Int. Cl.³ .......................................... H04N 7/18
[52] U.S. Cl. .................................. 358/106; 358/139; 358/213
[58] Field of Search ................ 358/106, 107, 214, 10, 358/139

[56] References Cited

U.S. PATENT DOCUMENTS

| | | | |
|---|---|---|---|
| 3,781,574 | 12/1973 | White et al. | 307/304 |
| 4,253,120 | 2/1981 | Levine | 358/213 |
| 4,264,930 | 4/1981 | White | 358/213 |
| 4,276,609 | 6/1981 | Patel | 364/900 |
| 4,344,091 | 8/1982 | Gardner | 358/213 |
| 4,367,492 | 1/1983 | Harada | 358/213 |
| 4,392,157 | 7/1983 | Garcia | 358/213 |
| 4,399,464 | 8/1983 | Hix | 358/213 |

OTHER PUBLICATIONS

"CCD Tracker for High Accuracy Guidance Applications," by Phil M. Salomon of Jet Propulsion Laboratory—received by applicant 6/16/80.
"Charge-Coupled Devices Tackle TV Imaging," by A. P. King & M. Farrier in Electronic Design, pp. 183–190, Aug. 6, 1981.
A ten-page brochure by Photometrics Ltd. of Tucson, Arizona describes a Model CH81-A camera head and Model 80A Universal Camera Controller, published prior to Jun. 1981.

Primary Examiner—Howard W. Britton
Attorney, Agent, or Firm—Eugene M. Whitacre; Dennis H. Irlbeck; Lester L. Hallacher

[57] ABSTRACT

A system for detecting blemishes on an illuminted object, such as the screen of a kinescope, includes a charge coupled device (CCD). The signal from each CCD pixel is compared with the average of the signals of all pixels immediately adjacent to the pixel being investigated to provide a difference signal. The difference signal is compared to a threshold level and a blemish signal generated when the difference signal exceeds the threshold.

7 Claims, 10 Drawing Figures

| P1 | P2 | P3 | P4 |
|----|----|----|----|
| P5 | P6 | P7 | P8 |
| P9 | P10 | P11 | P12 |

| 4002 | 4001 | 4004 |
|------|------|------|
| 4000 | 3600 | 4001 |
| 4002 | 4004 | 3998 |

| 3200 | 3047 | 2912 |
|------|------|------|
| 3105 | 3040 | 2902 |
| 3194 | 3032 | 2891 |

| 4001 | 4004 | 4004 |
|------|------|------|
| 3600 | 4001 | 4003 |
| 4004 | 3998 | 4001 |

Fig. 1a IDEAL BRIGHTNESS LEVEL

Fig. 1b PATTERN AFTER LENS

Fig. 1c PIXELS

Fig. 1d SIGNAL PER PIXEL

CHARGE COUPLED DEVICE BASED BLEMISH DETECTION SYSTEM AND METHOD

BACKGROUND OF THE INVENTION

This invention relates generally to systems and methods employing a charge coupled device (CCD) and particularly to such a system and method for detecting blemishes on the screen of a kinescope.

CCDs are used in conjunction with an optical lensing system which focuses the light from the object being investigated onto the CCD. Varying amounts of light on the individual pixels within the CCD charge the pixels to different levels proportional to the incident light. The optical information from the object is, therefore, available in analog form across the pixels of the CCD array. The analog information is then shifted out of the CCD and converted into digital form and stored in a digital memory where the various characteristics of the object can be checked or tested by the proper manipulation of the digital information. The individual pixels within a CCD array typically are closely spaced and are arranged horizontally in rows and vertically in columns so that a given CCD imaging device provides a fixed number of pixels of information. As an example, the SID52501 CCD presently available from RCA corporation has 320 vertical columns of pixels and 512 horizontal rows of pixels. Accordingly, the information is read out from the CCD and stored in 320 vertical columns and 512 horizontal rows.

Charge coupled devices have several characteristics which make them advantageous in imaging. CCDs are small and rugged and have closely spaced pixels and accordingly, are useful in applications requiring precise measurements. Additionally, a CCD receives an image by the direct reception of energy without being scanned, and stores the received data until the data are transferred to a storage device. Accordingly, a CCD can image a device which develops an image by scanning without concern for the scanning rate of the device being imaged. Also, the data received from the CCD can be processed by simple comparison or detection techniques so that the voluminous and time consuming sampling techniques ordinarily required for processing data from a scanned image are not required. For this reason, CCDs are advantageous in systems for testing color television kinescopes for blemishes and convergence.

The instant invention utilizes these advantages by the provision of a CCD based blemish detection system and method wherein the charge received by each pixel of the CCD is compared with the average charge received by all immediately adjacent pixels to provide a blemish signal when the comparison exceeds a preselected threshold.

CROSS REFERENCE TO RELATED APPLICATIONS

Application Ser. No. 388,143 entitled "CHARGE COUPLED DEVICE BASED INSPECTION SYSTEM AND METHOD:" filed of even date herewith by R. A. Duschl describes a system in which the claimed can be used.

SUMMARY OF THE INVENTION

A system for detecting blemishes on the screen of a kinescope includes a charge coupled device (CCD). The signal from each CCD pixel is compared with the average of the signals of the pixels immediately adjacent to the pixel being investigated to provide a difference signal. The difference signal is compared to a threshold level and a blemish signal generated when the difference signal exceeds the threshold.

BRIEF DESCRIPTION OF THE DRAWINGS

FIGS. 1a, 1b, 1c and 1d show how a blemish on a kinescope screen results in different charge levels on the individual pixels of a CCD array.

DETAILED DESCRIPTION OF THE PREFERRED EMBODIMENT

Figures 4A, 4B, 4C, 4D:
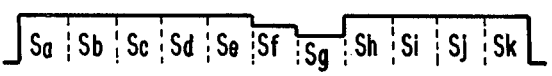
FIGS. 4a, 4b, 4c and 4d show how the charges on the pixels immediately adjacent to a particular pixel are averaged to detect a blemish.

FIGS. 1a through 1d show how a CCD is advantageous in detecting blemishes on the screen of a kinescope. A white field is generated on the screen of the kinescope and projected onto the CCD. The brightness across the screen varies somewhat from the edges to the center of the screen but is substantially uniform within any fractional area of the screen. Accordingly, in the absence of a blemish the signals generated on adjacent pixels are substantially equal. Thus, as shown in FIG. 1a, a substantially constant level brightness signal 15 from the kinescope screen illuminates the lensing system. A blemish of any sort which results in a dark spot on the screen causes a low spike 20 in the brightness level signal 15. A bright spot on the screen will cause a high spike in the signal 15 and for the purposes of this disclosure both of these conditions are defined as a blemish. The brightness signal 15 of FIG. 1a is projected onto the lensing system and the pattern 15a of FIG. 1b is received by the CCD. The lensing action rounds the sharp spike 20 of FIG. 1a into the rounded spike 20a of FIG. 1b. FIG. 1c shows the portion of one horizontal row of pixels Pa through Pk which receive the brightness signal 15a. FIG. 1d shows the charge levels Sa through Sk resulting on the pixels Pa to Pk respectively. The pixels Pa to Pe and Ph to Pk respectively are charged to substantially equal levels Sa to Se and Sh to Sk, which are proportional to the maximum brightness of the signal 15. The actual charge levels are dependent upon the brightness of the kinescope illumination. However, because of the averaging technique employed, the actual levels need not be utilized in describing the operation of the invention. The pixels Pf and Pg respectively are charged to the lower levels Sf and Sg because of the blemish induced spike 20a. Only pixel Pg would be charged differently if the lens system did not round the spike 20 so that the blemish may appear slightly larger than it actually is. However, the charge level of each pixel is equal to the area under the curve. Accordingly, differences between the Sf level and the other pixels are compensated for by the averaging techniques utilized in the inventive system. The close spacing of pixels within the CCD, therefore, makes it possible to detect very small blemishes on the screen of a CRT. Additionally, the CCD pixels receive and store charges proportional to the energy received from the kinescope screen without scanning the CCD in synchronism with the scanning of the screen. The data, therefore, can be processed for such purposes as blemish detection without using the complex sampling techniques required when a scanned type of sensor is used.

Figure 2:
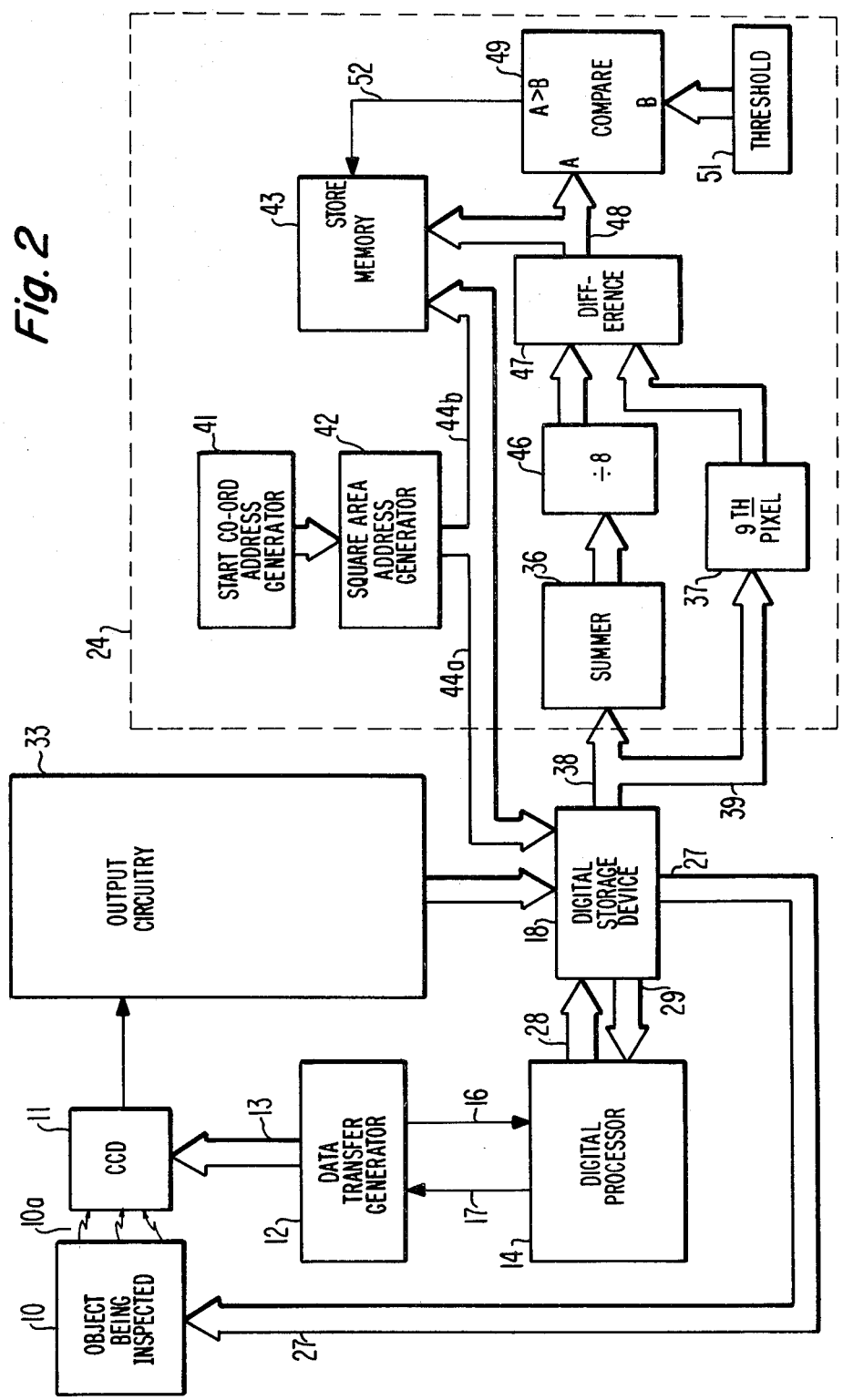
FIG. 2 is a CCD inspection system incorporating a preferred embodiment of a blemish detection system reduced to practice using hardware.

FIG. 2 shows a system including a charge coupled device (CCD) 11 for inspecting an object 10. The object being inspected preferably is a kinescope for a color television receiver and the inspection being performed is the detection of blemishes on the kinescope screen. The light rays 10a eminating from the screen of the kinescope 10 impinge upon the CCD and each pixel of the CCD is charged proportionately to the amount of light energy received. A data transfer generator 12 is coupled to the CCD 11 by output lines 13. The data transfer generator 12 transfers the analog information from the CCD to a frame store, or digital storage device 18. The transfer of the data from the CCD to the storage device 18 can be effected through output circuitry 33 in a manner described in Patent Application Serial Number 388,143 fully referenced hereinabove or in any other manner within the purview of one skilled in the art.

The generator 12 and a digital processor 14 communicate through two connecting lines 16 and 17. Also, the digital processor 14 communicates with the storage device 18 through the connections 28 and 29. The digital processor 14 can be a PROM, EPROM or RAM depending upon the flexibility and speed required for the particular inspection being performed. The digital storage device 18 also is coupled to the object being tested 10 by line 27. The digital storage device 18 also communicates with a blemish detection system 24 which is fully described hereinafter.

In operation the CCD 11 is exposed to the light rays 10a from the kinescope 10 being tested and each pixel within the CCD is charged proportionately to the amount of light inpinging upon the particular pixel. The CCD 11 acts as an analog storage device for the information received from the kinescope screen. The analog data available on the CCD 11 are read out to and stored in the digital storage device 18. The data stored in the storage device 18 are then processed by the blemish detection system 24 to reveal the presence of blemishes on the screen of the kinescope 10. The blemish can be caused by any fault which results in either a dark spot or a bright spot on the kinescope screen which is of sufficient brightness variation to be objectionable to the human eye.

In using the blemish detection system 24 the digital processor 14 is used to provide the digital storage device 18 with the signals which would be received from the kinescope 10 if an optimum white field were projected from the kinescope screen to the CCD 11. These signals are temporarily stored in the digital storage device 18 and are provided by the storage device 18 over the lines 27 to the kinescope 10 to generate a white field on the screen of the kinescope. The white field is projected onto the CCD and the data are transferred from the CCD by the output circuitry 33 and stored in the digital storage device 18. Prior to the transfer of the data from the CCD to storage device 18 the white field data are removed from the storage device. When the screen of the kinescope is imaged onto the CCD, the lensing system (not shown) which focuses the image onto the CCD focuses the white field so that the complete CCD is not utilized in imaging the white field. Accordingly, the peripheral vertical columns and horizontal rows of pixels of the CCD are not used in imaging the white field. The data received from each pixel of the CCD 11 are stored at a particular address in the digital storage device 18 and the location of the spot on the kinescope screen which produced the data is known.

The digital storage device 18 communicates with a summer 36 and a ninth pixel circuit 37 by way of the output lines 38 and 39, respectively. A start coordinate address generator 41 provides the address of the first pixel which is illuminated by the white field from the kinescope screen. A square area address generator 42 provides the addresses of the eight pixels which are immediately adjacent to, and which therefore surround a particular pixel of the CCD. These addresses are provided to the digital storage device 18 and a memory 43 by way of the output lines 44a and 44b, respectively. The signals received from the eight pixels are summed in the summer 36 and provided to a divider 46 where the sum is divided by eight to provide an average signal to a difference circuit 47. The signal from the ninth (particular) pixel is provided to the difference circuit 47 and subtracted from the average signal to generate a difference signal on the output line 48. The difference signal is provided to a comparator 49 which also receives a threshold signal from a threshold circuit 51. When the difference signal from the difference circuit 47 exceeds the threshold signal from the threshold circuit 51 a blemish signal is output to the output line 52 and provided to the memory 43. This blemish signal indicates that a blemish exists on the ninth (particular) pixel and because the address of the pixel is provided to the memory 43 the location of the blemish on the CRT screen is known. The address generator 41 is then incremented horizontally and if necessary, vertically one pixel and the process repeated for the next particular pixel, this operation continues until all pixels are investigated for blemishes.

FIG. 4a shows twelve pixels $P_1$ to $P_{12}$ of the CCD 11 of FIG. 2 included in portions of three horizontal lines and four vertical columns. In order to detect a blemish on pixel P6, the signal proportional to the charges on the immediately adjacent pixels P1, P2, P3, P7, P11, P10, P9, and P5 are provided to the summer 36 of FIG. 1 and divided by eight in the divider 46 to provide the average signal. The signal from the pixel P6 is provided by the ninth pixel circuit 37 to the difference circuit 47 and subtracted from the average signal. The threshold signal provided by the threshold circuit 51 is selected to accommodate differences in the signals received from the pixels which are not objectionable to the human eye and to make allowance for known differences in the characteristics of the various pixels of the CCD. The human eye is sensitive to brightness variations of 1%. The threshold level, therfore, is selected to permit difference signals which are less than 1%. When the difference signal exceeds the threshold signal the objectionable 1% brightness variation is present and a blemish signal is provided on the output line 52 and input to the memory 37. Thus, both the level of the blemish signal and the address of the particular pixel (P6) on which the blemish was detected are stored in the memory 43.

After the pixel P6 is compared to the average of the immediately adjacent surrounding pixels, the start coordinator generator 41 sequentially provides the addresses of pixel P7 and the eight surrounding pixels to the digital storage device 18 and to the memory 43. The average value of the signals received from the immediately adjacent pixels P2, P3, P4, P8, P12, P11, P10 and P6 is then compared to the signal received from the pixel P7 to determine whether or not a blemish exists at the location on the kinescope screen detected by pixel P7. This operation continues until the entire white field on the kinescope screen is investigated a pixel at a time. The peripheral horizontal rows and vertical columns of pixels, such as P1 through P4 and P1, P5, P9 if the portion of the CCD array shown in FIG. 4a were a corner, are not investigated because these pixels are not completely surrounded by other pixels of the CCD array. However, these pixels are outside the viewing area of the kinescope screen and accordingly the presence of blemishes on these pixels is not objectionable.

FIG. 4b is useful in understanding how the averaging technique operates. The numbers in the pixels are arbitrarily assigned values which correspond to the measured brightness signals on the screen of a kinescope. The exact values are dependent upon the brightness level to which the kinescope is driven and upon the calibration of the system Accordingly, the actual numbers used herein are exemplary only and the selection of actual values used in a system is within the purview of one skilled in the art. For the numbers chosen the threshold value is set at 100, which is substantially lower than the 1% variation to which the human eye is sensitive. The average signal of the eight surrounding pixels is 4002, and the value in the particular pixel under investigation is 3600. The difference signal, therefore, is 398, which exceeds the threshold level of 100. Accordingly, a blemish signal is provided to the memory 43 (FIG. 2), and the level and location of the blemish are known. The charge on the pixel being investigated was below the average charge indicating that the blemish is a dark spot. If the signal in the particular pixel were 4400 the difference signal would be the same magnitude and a blemish resulting from a bright spot would be indicated.

FIG. 4c shows how the system automatically compensates for the natural shading of the brightness across a kinescope screen. The values in the pixels of FIG. 4c are substantially less than those in the pixels of FIG. 4b. The difference in charge levels occurs because the brightness across the face of a kinescope screen is not uniform and is lower toward the edges of the screen than at the center of the screen. Even although it is in excess of 1% the change of brightness is gradual rather than abrupt and therefore is not detectable by the human eye and is not objectionable. By comparing the signal received from each pixel with the signals received from the immediately adjacent eight pixels the natural kinescope shading is automatically compensated for. In FIG. 4c, the average signal received from the eight surrounding pixels is 3048 and the signal received from the particular pixel is 3040. The difference between the average signal and the central pixel signal is eight and is below the threshold level of 100. A blemish, therefore, is not indicated even though the investigation was made at a low brightness portion of the screen. Accordingly, the brightness variations caused by the shading on the CRT screen are compensated for by the averaging system.

FIG. 4d shows that the presence of a blemish in one of the averaging pixels does not adversely affect the investigation of another pixel. In FIG. 4d, the two left-hand columns of pixels are identical to the two right-hand columns of pixels of FIG. 4b. Thus, FIGS. 4b and 4d respectively represent the sequential investigation of pixels P6 and P7 of FIG. 4a. In FIG. 4d when the pixel having a value of 3600 and which previously was found to have detected a blemish, is included as one of the eight adjacent pixels the average signal is 3951. The signal of the particular pixel is 4001. The difference signal of 50 is lower than the threshold value of 100 and the averaging technique is accurate even when a pixel which detects a blemish is included in the averaged pixels. If desired, the presence of a blemish can be verified by the use of standard sampling techniques.

Figure 3:
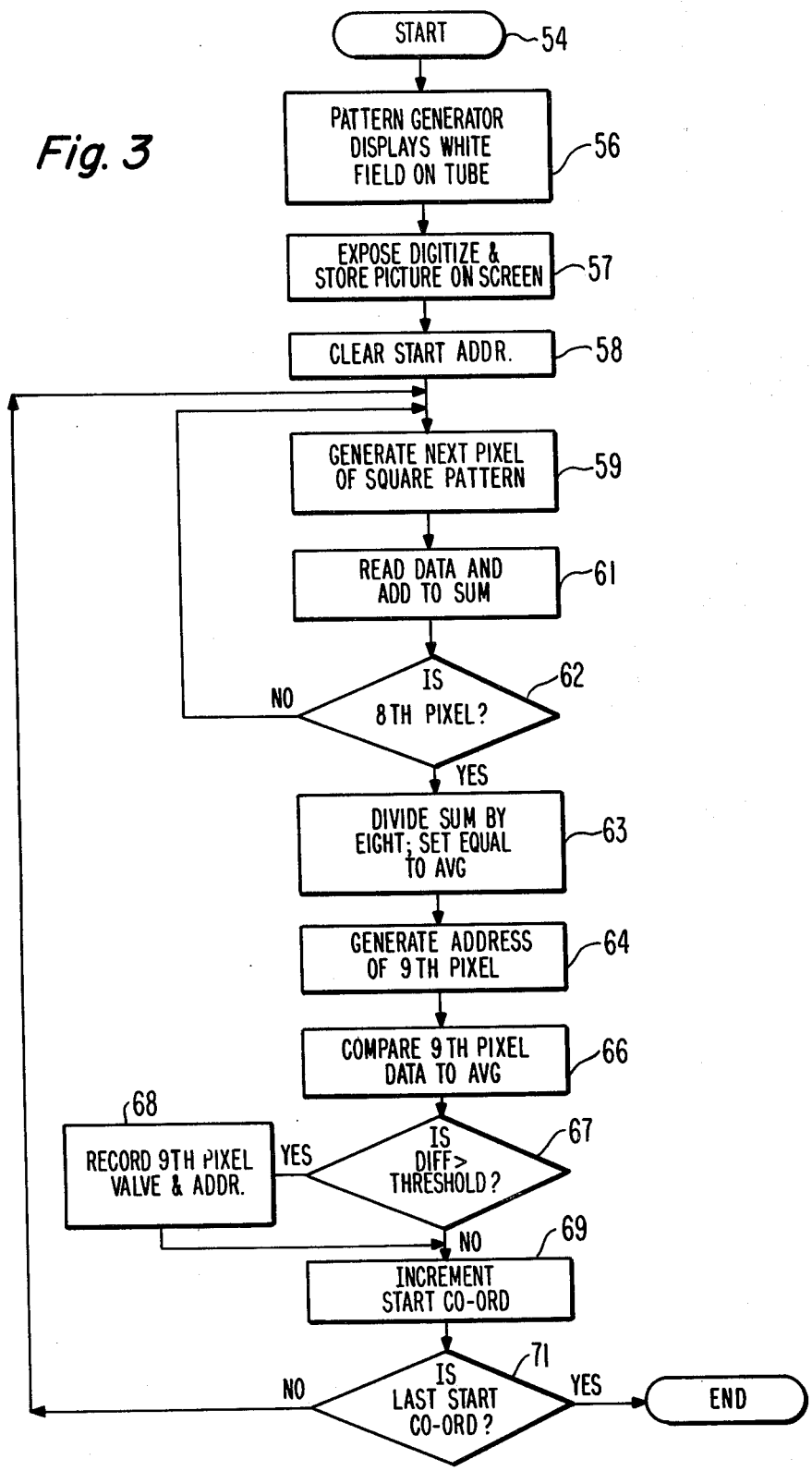
FIG. 3 is a flow chart of a preferred embodiment of a blemish detection system reduced to practice using software.

FIG. 3 is a flow chart of a preferred embodiment when the blemish detector 24 of FIG. 1 is reduced to practice using software. Accordingly, when the digital processor 14 has sufficient memory capacity the blemish detection functions can be carried out in the processor 14. In FIG. 3, the start function 54 and function 56 are entered and the digital processor 14 provides an input to the digital storage device 18 to generate the white field on the screen of the kinescope being inspected. At functional block 57, the CCD is exposed to the white field and the signals from the CCD are transferred from the output circuitry 33 to the digital storage device 18. At functional block 58, the digital storage device 18 is addressed and the starting pixel address is supplied. This is the pixel in the upper left corner of the nine pixel area under investigation. At functional block 59, the addresses of the eight pixels which are immediately adjacent to the ninth pixel to be investigated are generated. At functional block 61, the data from the eight pixels are read and added to provide a sum signal. After the signals from the eight pixels are added, the sum is divided by eight and set equal to an average signal at functional block 63. At functional block 64, the address of the ninth pixel is provided and at functional block 66, the signal from the ninth pixel is subtracted from the average of the surrounding eight pixels to provide the difference signal. The difference signal is compared to the threshold value at functional block 67, and when the difference signal is greater than the threshold level, the address and signal value of the ninth pixel is stored at functional block 68. If desired, the presence of a blemish can be verified by using standard sampling techniques in the close vicinity of the detected blemish. When the difference signal is not greater than the threshold value, functional block 69 is entered to increment the address counter and to start the coordinate address. At functional block 71, if it is the last start coordinate, the routine is ended and if it is not the last start coordinate, the functional block 59 is returned to sequence the system to the next pixel to be investigated.

What is claimed is:

1. A system for detecting blemishes on an illuminated object comprising:
   a digital storage device;
   a charge coupled device (CCD);
   output circuitry for transferring data from said CCD to said digital storage device, whereby the data from each pixel of said CCD is stored at a specific address within said digital storage device;
   means for averaging the signals from the adjacent pixels surrounding a particular pixel and providing an average signal;
   address generator means for providing the address of the square area containing said adjacent pixels to said digital storage device to transfer the signals from said adjacent pixels to said means for averaging;

means for receiving the particular signal from said particular pixel;

means for receiving said average signal and said particular signal and providing a difference signal representative of the difference between said average signal and said particular signal;

means for providing a threshold signal representative of the permissible maximum of said difference signal; and comparator means for receiving said difference signal and said threshold signal and providing a blemish signal when said difference signal exceeds said threshold signal.

2. The system of claim 1 further including memory means responsive to said address generator means and to said comparator means for storing the address of said particular pixel when said blemish signal is generated.

3. The system of claim 2 wherein said means for averaging includes means for summing said signals from said adjacent pixels and means for dividing said sum by eight.

4. The system of claim 1 or 2 or 3 wherein said illuminated object is a kinescope and wherein digital storage device provides an output for generating a white field on said kinescope screen prior to receiving data from said CCD.

5. A method for detecting blemishes on an illuminated object comprising the steps of:

generating an illuminated field on the screen of said object;

imaging said field with a CCD and transferring the CCD data to a digital storage device wherein the data from each pixel of said CCD is stored at a different address;

averaging the data from the immediately adjacent pixels surrounding a particular pixel to obtain an average signal;

taking the difference between the data from said particular pixel and said average signal to obtain a difference signal;

comparing said difference signal to a threshold signal and providing a blemish signal when said difference signal exceeds said threshold; and providing said blemish signal to a memory to store the address of said particular pixel whereby the location of the blemish which caused said blemish signal is known.

6. The method of claim 5 wherein said object is the screen of a kinescope and said illuminated field is a white field on the screen of said kinescope, and wherein there are eight of said adjacent pixels.

7. The method of claim 5 or 6 further including the step of ignoring the data from the pixels contained in peripheral rows and columns of said CCD.

* * * * *